United States Patent [19]

Sattler

[11] Patent Number: 4,906,083

[45] Date of Patent: Mar. 6, 1990

[54] APPARATUS FOR EXAMINING GEMSTONES AND THE LIKE

[76] Inventor: Hans-Eberhard Sattler, Oderstrasse 63, D-5300, Bonn 1, Fed. Rep. of Germany

[21] Appl. No.: 197,262

[22] Filed: May 23, 1988

[30] Foreign Application Priority Data

May 21, 1987 [DE] Fed. Rep. of Germany ....... 3717051
Nov. 9, 1987 [DE] Fed. Rep. of Germany ....... 3738041
Jan. 28, 1988 [DE] Fed. Rep. of Germany ....... 3802535

[51] Int. Cl.$^4$ ..................... G02B 21/06; G02B 21/34; G01N 21/00
[52] U.S. Cl. .................................. 350/524; 350/536; 356/30
[58] Field of Search ............... 350/507, 510, 514, 523, 350/524, 536, 406, 529, 534, 535; 356/30, 31

[56] References Cited

U.S. PATENT DOCUMENTS

| 2,318,705 | 5/1943 | Morgan | 350/510 |
| 2,869,417 | 1/1959 | Allen . | |
| 3,554,631 | 1/1971 | Beyer et al. | 350/534 |
| 3,963,348 | 6/1976 | Nakatani et al. | 250/223 B |
| 4,226,534 | 10/1980 | Kuck | 350/529 |
| 4,505,555 | 5/1985 | Piller et al. | 350/527 |

FOREIGN PATENT DOCUMENTS

| 0147002 | 7/1985 | European Pat. Off. . |
| 1958962 | 2/1967 | Fed. Rep. of Germany . |
| 2444644 | 4/1976 | Fed. Rep. of Germany . |
| 3602095 | 7/1986 | Fed. Rep. of Germany . |

OTHER PUBLICATIONS

"Bestimmungen von Edelstein mit Edelsteinkundlichen Geräten", (Determination of Gemstones using Gemological Devices), Godehard Lenten, pp. 200–201.
Published data sheet of Plexiglass TM manufactured by Röhm GmbH.
Brochure from System Eickhorst, Gemmodul MS, 2000 Hamburg 76, Hans-Henry-Johann-weg 21.
Brochure from Sortoscope by Nissigem, Nossigem Lab-Service, Dr. Eberhard Sattler FAA, Buchholzstrasse 2, 5300 Bonn 1.
Article by Will Kleber, UEB, Verlag Technik, Berlin,
"Einfuhrung in die Kristallographic", 10th Ed., 1969, pp. 296–300.
"The Cargille-Allen Gem Testing Set", published by R. P. Largille Laboratories, Inc., 117 Liberty St., New York, NY.
Brochure from System Eickhurst, Gemmscope, 2000 Hamburg 76, Hans-Henry-Johann-weg 21.
"Gems, Their Descriptions", R. Webster, 4th ed., pp. 540–542.
Praktisobe Gemmologie Ruble-Dieben, pp. 451–463.
Brochure "Miniature Magnetic Positioning Cube", Feb. 1, 1972, Titan Tool Supply, Inc., Buffalo, NY.
Edelsteine und Perlen, Prof. Dr. Karl Schlossmacher, 5th Edition, E. Schweitzer'sche Verlagsbuchhandlung, Stuttgart, 1969, pp. 101–104.

Primary Examiner—Bruce Y. Arnold
Assistant Examiner—Ronald M. Kachmarik
Attorney, Agent, or Firm—Spencer & Frank

[57] ABSTRACT

An apparatus, particularly a microscope, for the examination of a plurality of gemstones, pearls or similar small objects, comprises means to create dark-field illumination and a slide-type displaceable specimen holder of plastics material which has an elongate recess in its upper surface with a cross-section which narrows towards the bottom of the recess for example. The means to create the dark-field illumination comprises a cold light source, a glass-fiber bundle and polarization filter means, and the specimen holder consists of translucent material, especially Plexiglass. Additionally there is provided a device for aiding the examination of uncut gemstones and similar small objects, comprising means to create dark-field illumination and means for immersion inspection which comprises a vessel containing an immersion liquid. This vessel is equipped with a damping float of transparent material having a flat base and an open upper end, which in the operational position of the apparatus is inserted into the immersion liquid and floats therein, with the base of the damping float having a surface which is at least as large as the object to be examined.

33 Claims, 4 Drawing Sheets

APPARATUS FOR EXAMINING GEMSTONES AND THE LIKE

BACKGROUND OF THE INVENTION

1. Field of the Invention

The invention relates to apparatus, in particular a microscope, for the examination of a number of gemstones, pearls or similar small objects, comprising means for creating dark-field illumination and a slide-type displaceable specimen holder of plastics material which has an elongate recess in its upper surface.

2. Description of the Prior Art

It is known to inspect gemstones or crystals using a magnifying lens or a microscope. The illumination is created either according to the transmitted-light principle or the incident-light principle. In the first case the light passes through the transparent or translucent object, while in the second case the object is illuminated from the side and the reflected light rays are gathered. The object being examined can be observed against a light field or against a dark field in the case of illumination according to either of the aforesaid principles. In the case of light-field illumination the background appears bright and the object dark, while with dark-field illumination the object appears bright and the background appears dark.

For the examination of gemstones it is also known to use microscopes (commonly microscopes having nipples as object holders) equipped with polarization optics, i.e. with a polarizer and an analyzer. In order better to be able to observe light refraction, reflection and total internal reflection at the facets of gemstones, in many cases transmitted-light, dark-field illumination is used, in which the object is illuminated from the side or the central zone of the illuminating light beam is screened out.

For the examination of particular objects, such as for example uncut gemstones, which are rough and without defined crystal faces, it is necessary to inspect these objects in an immersion liquid. The refraction and total internal reflection phenomena arising from the different refractive indices of air and specimen can in this way be at least greatly reduced, depending upon the actual refractive indices, thus producing a picture which is closer to reality. However, with this method of examination, damage to or flaws in a gemstone are not outwardly visible. For the examination of a series of features of gemstones, such as for example double refraction, perhaps observation of double-refractive inclusions, as well as stresses, the use of polarized light is indispensable. With crossed polarizers, double-refracting crystals appear bright, while single-refracting crystals remain dark (see also the article by Will Kleber, VEB Verlag Technik Berlin, "Einfuhrung in die Kristallographie", 10th Edition, 1969, pages 296 to 300).

The provision of vessels containing immersion liquid in the vertical light beam path of microscopes has proved to be disadvantageous for various reasons. First of all, small glass beakers of about 2cm depth have been used, which are positioned on the illuminating aperture of the microscope stage. Upon movement of this glass beaker it can happen that the immersion liquid, which is extraordinarily aggressive chemically, can spill over and lead to corrosion and damage to the optics. A further disadvantage of such immersion systems is that, as a result of movement of the liquid or of the liquid surface, one obtains a blurred image. For these reasons, for the examination of objects in immersion liquid, microscope systems have been developed in which the light beam travels horizontally through the immersion liquid. In this so called "German" system movement of the liquid surface does not impair the examination process.

For the displaying of large batches of gemstones, particularly for the dimensional analysis of gemstones of average quality, so called sorting boards of plastics material are used. The gemstones are arrayed on these sorting boards and the array is examined from above in order to observe the effect of the stones. Higher quality stones on the other hand are viewed from below, for example in order to observe the cut of the gem.

In U.S. Pat. No. 3,554,631 there is described a specimen holder, particularly for interference microscopes, which is provided with a groove which tapers down towards the base. The width of the groove at the upper surface is $\simeq 100$ $\mu$m and at the bottom is approximately 10 $\mu$m. The dimensions of the groove are so chosen that the interference rings can be observed individually over the whole width of the groove, with the width of the groove at the upper surface of the specimen holder preferably being smaller than the diameter of the object field. This permits the interference rings to remain fully visible during the whole measuring process and to have approximately the same spacing from each other at the bottom of the groove.

In one microscope described in DE-GM 1 958 962 there is used a system having dark-field illumination and a slide-type displaceable specimen holder of transparent plastics material. Below the specimen holder is positioned an incandescent lamp, the light from which travels either directly to the specimen holder or first to a reflector laterally surrounding the lamp and thereafter to the specimen holder. Between the incandescent lamp and the specimen holder there is positioned a diaphragm. If the diaphragm is open, then the light rays can strike the specimen holder directly and perpendicular to its surface, while if the diaphragm is closed the light rays from the reflector strike the specimen holder at an angle. Additionally, this known microscope comprises a fluorescent lamp for the incident-light illumination, in order to improve the visibility of mineral inclusions in gemstones for example. Such incident-light illumination also makes it possible to inspect diamonds.

The specimen holder of this known microscope is formed as a displaceable rail with indentations, in order to be able to examine a number of gemstones in succession. For the displacement of the rail it is proposed to provide a manually actuated knurled wheel, with this wheel preferably being positioned outside the field of view. This leads however to an elongation of the means used to hold the specimen holder in place. For a stepless displacement of the specimen holder it is preferred to use a friction drive which can consist for example of a rubber roller, a belt pulley, a belt and a knurled wheel.

In its upper surface the specimen holder is provided with the aforesaid recess which as a rule consists of two channels (indentations) having a V-shaped cross-section. The side faces of the channels preferably are each set at 45°, so that they together form an angle of 90°. The gemstones are arranged at the beginning of the examination process with the known microscope in one of the two channels and are moved, after appropriate sorting, into the other free channel. For the observation of the gemstones the diaphragm is closed, so that only indirect rays strike the specimen holder from below, with the result that only the channels are lighted. This means that only the stones are struck by the rays and the remaining surfaces appear dark.

However, the known microscope described above has considerable disadvantages in practical use. The incandescent lamp used for illumination gives rise on the one hand to a considerable heating of the specimen holder and on the other hand the luminosity which it produces is not satisfactory, even with the use of a 60 watt lamp. For this latter reason the inclusion of a polarization system is not possible. The specimen holder is heated to more than 60° C., even with the use of an electric bulb of about 30 watts. It is also a particular disadvantage that plastics materials such as Plexiglas for example are poor conductors of heat, so that the illuminated underside of the specimen holder is noticeably warmer than the upper side. This leads to a deformation or stressing of the specimen holder, with the result that its capacity to slide and be displaced are substantially impaired and, in some circumstances, possibly after several hours use of the system, it is no longer usable.

Microscopes in which a glass-fiber cable is used for the purpose of illumination are known. In one such microscope as described in U.S. Pat. No. 4,505,555 a glass body is positioned close to the end surface of a glass-fiber cable and serves to pick up the light transmitted by the glass-fiber cable and to transfer light to the output surface with a uniform light intensity distribution. The light beam which is thus created is then passed into the optical system of the microscope.

In the case of pearls, which are basically divided between natural pearls and cultured pearls, these look practically the same when viewed externally, but nevertheless have very different monetary values. In order to be able to distinguish between natural and cultured pearls, an instrument known as a lucidoscope has been developed for example, in which the pearl is immersed in an immersion solution, is irradiated by a strong light source, and is observed through a microscope. If the pearl under examination is a cultured pearl, then with suitable orientation of the pearl, striations of the mother-of-pearl core are visible. However, this effect only occurs occasionally, so that this instrument is not really suitable for the examination of cultured pearls, and especially not for such pearls which are covered by thick scale. Furthermore, it is disadvantageous that one has to have considerable screening due to the strong light source, and also that because of the need to use the immersion liquid one cannot examine strings of pearls or the like. Other methods of examining pearls have been based on the use of X-rays, X-ray refraction pattern processes and X-ray shadow image methods (see for example Schlossmacher, "Edelsteine und Perlen", Stuttgart, 1969).

SUMMARY OF THE INVENTION

It is an object of the present invention to provide a device for the examination of a number of gemstones, pearls or other small objects by means of which it is possible to examine, and possibly sort out a quantity of gemstones, etc. rapidly and reliably.

This object is achieved in accordance with the invention in an apparatus of the type first referred to above in which the means for dark-field illumination comprises, as a light source, a cold light source with a glass-fiber bundle and also polarization filter means, and in which the specimen holder is formed of translucent material, in particular Plexiglas. The term "translucent material" used herein should be understood as meaning a material which is not clear.

The apparatus of the invention is distinguished by an advantageous combination of a light source, polarization filter means and specimen holder. The use of a cold light source, such as a halogen lamp for example, makes it possible to achieve illumination with an extraordinarily strong intensity, with the glass-fiber bundle being able to take care of the concentration of the light rays from the outset. There follows from this the examination of the gemstones etc. with crossed polarization filters. From the observed object—so long as it is an optically isotropic crystal or an amorphous substance—one obtains elliptically polarized light which, because of the strong light source, has a sufficient intensity for the examination of gemstones or pearls. Commonly, a magnification factor of 10 to 50 (100) is chosen.

Preferably, the elongate recess is shaped to have a cross section which narrows towards the bottom of the recess. This makes it possible to achieve a particularly favorable and stable arrangement of the stones in conformity with their cut.

The illumination of the objects to be examined is determined among other things by the angle of incidence of the light rays, the amount of light which is available and the distance between the light source and stones. In the case of a strong light source a more unfavorable angle (in alignment with the angle of total internal reflection) can be chosen, since even then a sufficient amount of light will be present for the examination procedure. Then, a more favorable wedge angle can be chosen for the positioning of the specimens in the recess of the specimen holder. Furthermore, a translucent, e.g. slightly milky, specimen holder can also be used. By varying the parameters, an optimum arrangement can be found for each case. If double-refracting stones are to be examined with the microscope of the present invention, then, because of the high intensity of the light passing through the stones, a dimmer is preferably incorporated into the system in order to reduce the light.

The distance between the light source and the particular stone which is under observation and the cross-section of the glass-fiber bundle are preferably so chosen that a relatively small light cone is produced with a cross section which is not too large, i.e. the beam spot is small, for example 6 mm$^2$. For these reasons one should preferably choose a cross section for the glass-fiber bundle of from 4 to 5 mm$^2$, preferably 4.5 mm$^2$. In this way it is possible, after examining a particular gemstone or a particular pearl, to find this object again on the specimen holder with the aid of the beam spot. The beam spot thus fulfills a marking function.

The material of the specimen holder and the angle of inclination of the walls of the elongate recess for the specimens are chosen in accordance with the gemstones, etc. which are to be examined. The less transparent the stones are, the more light-permeable must the material of the specimen holder be. Plexiglas has proved to be a particularly suitable material.

In the case of colored stones, Plexiglas of Type 010, a brand of the plastic polymethylmethacrylate manufactured by Royhm GmbH, Darmstadt, Federal Republic of Germany, is preferably used. This material is 66% translucent. The light which passes through it is substantially polarized or partially polarized. The preferably channel-shaped recess has a wedge-shaped cross section and the side walls form an angle of between 90° and 120°, preferably 100°, with each other. With this wedge angle one achieves a more favorable working point in terms of the position of the stone in the recess and the light transmission in the stone. If the angle is smaller, when less light enters the specimen, while with a larger angle, although it is true that more favourable optical properties result, the stone is then in a sloping position and the possibilities for examination are poorer.

If brilliants (diamonds) are to be examined with the microscope of the present invention, then the material of the specimen holder is preferably Plexiglas of Type 072, manufactured by Rohm GmbH, which is 24% translucent and therefore milky. The light passing through a specimen holder of such material is diffuse and not polarized, which is attributable to stray (scattered) particles which are present in this type of Plexiglas. It is then desirable to incorporate a daylight filter arrangement intermediate of the polarization filters which makes possible a true color reproduction of the brilliant tones (as the different yellow tones). The side walls of the channel-shaped recess preferably have a wedge-shaped cross section with a wedge angle of between 80° and 90°, preferably an angle of 85±2°. This ensures a reliable centering of the brilliant in the recess in this arrangement and a favorable arrangement for the examination. An angle of 90° is not desirable for optical reasons, while with an angle of 80°, 30% more time is needed for the alignment of the brilliants in the observation position, i.e. they must be agitated longer. It is desirable to reduce the agitation time.

Instead of Plexiglas of type 072, Plexiglas of Type 010 can alternatively be used for the examination of brilliants. This makes it possible to obtain a more accurate examination of inclusions. However, the image is less accurately true to color.

By means of the apparatus of the present invention all inclusions in stones etc. can be seen, without relative rotation, as well as is possible conventionally with an immersion microscope. For this it is only necessary to adjust the depth of focus, so that the viewing is carried out in corresponding planes. Simultaneously, one can also determine cut features and flaws in the cut of the gemstones, even on their underside, and both also at a glance.

In the case where the material of the specimen holder is to be made opaque, the side wall surfaces of the recess or the underside of the specimen holder or all these surfaces are made matt. Plexiglas of Type 010 is normally used additionally matt, with the result that the slide itself is not seen in the examination and the honeycomb pattern of the glass-fiber bundle is not visible. Only with special examination is such additional dulling of the surface not possible, for example if fine stripe structures in gemstones are to be examined.

It is possible with the apparatus of the present invention accurately to distinguish between natural pearls and cultured pearls without the use of X-ray methods. With the use of a specimen holder of Plexiglas 010 and crossed polarization filters the striations of the mother-of-pearl core of cultured pearls can be observed. The striations appear as alternating reddish and greenish iridescent bands. If, as in the majority of cases, no striations are visible, cultured pearls show iridescent green and red zones in a wide variety of different forms. Occasionally even these zones are missing, and then the edge zone appears light brown with light green spots. Natural pearls on the other hand exhibit none of these iridescent greenish or reddish zones but are pure ochre colour up to mid-brown without green spots. This quite different overall impression enables one to be able to distinguish reliably between natural and cultured pearls.

The specimen holder of the microscope of the present invention is preferably made in the following way. First of all, a specimen holder bar is cut and a wedge is milled in it at the desired angle. Then, the specimen holder is pushed back and forth on a metal block in order to remove roughness caused by the milling. It is additionally rubbed smooth using 1200 gage abrasive paper, so that a smooth guidance of the specimen holder is ensured when it is displaced relative to the microscope stage. The dulling of the upper surface of the specimen holder is provided by parallel grinding which however is only carried out of the aesthetic effect. The contact bearing surfaces themselves are polished flat by the manufacturer. A finish grinding leads to a tolerance of for example 5/10 0mm. The contact bearing surface of the specimen holder is chosen to be as small as possible, so that there is only a little friction upon displacement of the specimen holder. The centering of the pearls or gemstones in the case of colored stones is not so critical as with brilliants, so that the wedge formation can in the former case be made with somewhat less rigid tolerances.

The length of the specimen holder is optimised because of the prealignment of the stones carried out on the specimen holder before it is inserted into the microscope stage. This prealignment of the stones is carried out in the following way. The stones are first scattered into the elongate recess. Then, the specimen holder is gripped manually at one end and is slightly raised, so that it is in contact with the underlying support essentially only at the opposite end. Then the specimen holder is shaken back and forth which leads with slight elliptical rotation to a transverse movement of the stones. By this back and forth movement the stones are displaced in the recess in such a way that after the shaking approximately 95% of the gemstones arranged in the recess are arranged with their cut face upwards. The rest of the stones can then be properly aligned using forceps. Consequently, the person carrying out the presorting by the shaking process is subjected to as little tedium as possible. However, care must be taken that the specimen holder is moved with as little friction as possible on the supporting surface. It has proved to be desirable that a supporting surface should be chosen which is not a perfectly flat surface such as glass but which rather is undulating. This leads to the fact that the contact surface between support and specimen holder is smaller and the force necessary to carry out the shaking process is smaller. A support material which is suitable for this purpose is for example "Trespa" Vollkern with a thickness of at least 8 mm. "Trespa" is a Registered Trade Mark for an aminoplastic resin, particularly a melamine resin. "Trespa" Vollkern is a resin material having a surface which is profiled, not smooth, to reduce the contact surface area. Preferably, the wedge faces and contact bearing faces are polished. The contact bearing surface of the specimen holder is smoothed. Preferred dimensions for the recess in the specimen holder are a width and a depth of a maximum 7 and 3 mm respectively. The central recess in the underside of the specimen holder is preferably milled to approximately 5/10 mm. The specimen holder itself preferably has a length of about 30 cm, a width of about 3 cm and a thickness of about 0.6cm. The apparatus of the invention is well suited to the examination of chains of pearls or chains of gemstones. In such cases a longer specimen holder, for example approximately 50 to 60 cm long, is used.

In order to be able to examine larger stones or brooches a somewhat thicker specimen holder (for example about 0.7 cm) is particularly suitable, so that the object being examined does not come into contact with the microscope stage. In order to broaden the specimen holder one can suitably use a plate which is fixed to it.

In order to be able to displace the specimen holder in the microscope stage a dovetail guide is preferably formed in the microscope stage. This ensures a reliable and accurate guidance of the specimen holder in such a way that the pearls or gemstones can be reliably examined one after another and located again as necessary. In order to reduce the friction, the cut-out of the dovetail guide in the microscope stage is preferably formed in such a way that on each side a narrow support shoulder extends in the lengthwise direction adjoining the corner angle and on which the specimen holder is guided. In this way the contact bearing surface, and consequently the friction, is reduced. Alternatively, the specimen holder itself can be provided at its underside, at the edge, with for example a strip-like contact bearing surface in order to reduce the contact surface area.

It should be understood that, in the usual way, the apparatus of the present invention is suitable for the additional provision of incident-light illumination. This is used, as with any microscope, for the examination of non-transparent stones or to aid in the external illumination of edges or corners and the like. If the apparatus is to be used for particular examinations without transmitted light, then a light-impermeable disc or plate can be inserted into the transmitted light path.

The microscope of the present invention makes it possible to carry out an extremely rapid examination of gemstones or pearls. For example, it is possible to align approximately 100 small brilliants or brilliant chips in about 2 minutes by using the aforesaid jarring and shaking movement. For the cataloging of these thus aligned stones in the microscope only one and a half minutes are needed, so that the examination of the stones is completed within approximately three and a half minutes. Thus, one person can examine a total of about 12,000 brilliants in one seven hour working day. Fatigue is considerably reduced, because for one thing the presorting using the specimen holder is made easy with extraordinarily small frictional resistance and for another thing the optical conditions are extraordinarily easy on the eye because of the advantageous dark-field illumination of the invention.

The specimen holder itself can be displaced gradually by hand without difficulty because of the low friction, so that the stones can be examined one after the other in succession. About 100 stones can be arranged on a specimen holder having a length of about 30 cm, so that the individual stones are spaced from each other by a distance equal to about 3 mm. A displacement corresponding to this distance is possible without any problems and the light cone illuminates a surface area which is slightly greater than the size of any one stone. Because of the relatively small beam cone, particular stones, as desired, can be extracted by means of the forceps after the examination process.

If a scale or appropriate markings are provided on the specimen holder, for example on one half of it, then the stones etc. do not need to be removed immediately after a visual inspection, but one can instead note the marking corresponding to the particular stone position and remove that stone later. In this way eye dazzle is avoided.

For stones singled out in this way an intermediate repository on the microscope stage itself has proved to be desirable. The common black oxidized microscope stage has an adhesive label pasted on to it and this is marked using a fiber-tipped felt pen with marks which can subsequently be removed with a readily available alcohol-based liquid for example. This method may or may not be appropriate depending upon the number of stones singled out (about 3% for example). In the case of brilliants, these are picked up and removed by means of a so-called gathering forceps, while colored stones can be picked up by means of a pair of straight forceps and placed on the intermediate repository because of the larger wedge angle. The transfer of the extracted stones from the intermediate repository to a further repository can be carried out for example by means of forceps formed in the manner of a shovel or scoop. This can be accomplished successfully by the following measures. The microscope stage is provided at the upper external edge with a radial recess which is open upwards. The shovel-type forceps can then be manually held without strain against the substantially horizontal shoulder and then make contact with the vertical section of the recess. With a pair of forceps held with the other hand the objects which have been singled out can then be transferred to the shovel.

As mentioned above, certain gemstone examinations have to be carried out using immersion liquid. Frequently however it is too expensive to equip any one microscope or a corresponding apparatus for examination either with or without immersion liquid, so that it is desirable, even with a standard microscope with vertical beam path, to be able to inspect objects in an immersion liquid with sufficient optical quality. This is also possible with an apparatus according to the invention, as has been described above. It is therefore a further object of the invention to provide a device for the examination of objects in an immersion liquid which makes it possible to carry out this observation within a vertical beam path of for example a microscope.

This object is achieved in accordance with the invention by apparatus, particularly for examining uncut gemstones and similar small objects, comprising means to create dark-field illumination and a device for immersion examination comprising a vessel containing an immersion liquid, characterised by a damping float of transparent material having a flat base and an open upper end and which in the operational position of the apparatus is inserted into the immersion liquid and floats therein, wherein the base of the damping float has a surface which is at least as large as the object to be examined.

Preferably, the means to create the dark-field illumination comprises a cold light source as the light source, together with a glass-fiber bundle and polarization filter means. In this way undesirable dazzle effects can be excluded.

The apparatus of the present invention for examining objects in an immersion liquid is extraordinarily simply constructed. In essence it requires only two components, namely a vessel for the immersion liquid and a further component, namely the damping float, which has a flat transparent base and is made of suitable material. The damping float, after introduction of the object to be examined into the immersion liquid, is inserted into the liquid and sinks into the liquid according to the relative densities and then floats therein. The dimensions of the damping float are such that the base has a sufficiently large surface for examining the object, and the ratio of the base surface to the internal surface of the vessel containing the immersion liquid is sufficiently great in order effectively to achieve a calming of the liquid surface.

Plexiglas ($n=1.5$; density 1.18 g/cm$^3$) has proved to be a particularly favorable material for the damping float. The resistance of Plexiglas to immersion liquids has been investigated, where this material has been placed for a month in the particular immersion liquid and has thereafter been examined for loss of weight or dimensional changes. Other than for example in the case of polystyrene, the investigations prove that Plexiglas is sufficiently resistant for example to benzyl benzoate, i.e. benzoic acid benzyl ester ($n=1.57$; density 1.12 g/cm$^3$) and is resistant to bromonaphthalene ($n=1.66$; density 1.48 g/cm$^3$), these being the immersion liquids which are currently utilised.

One particularly simple form of damping float, although other shapes are obviously possible, is one where it is of cylindrical shape. In this case it can be formed simply as a cylindrical tube which is closed by a base. The base can either be fixed to the cylinder by adhesive or can be made integrally with the cylindrical tube.

In order to prevent the damping float tilting or becoming skewed in the vessel containing the immersion liquid, the damping float preferably has lateral spacer elements, preferably at at least three positions around its circumference. The use of for example three vertical ribs which extend over the full axial length of the float or over part of the length of the float has proved to be particularly advantageous. The spacer elements can be secured simply to the float wall or alternatively can be made integrally with the float.

Preferably, the vessel containing the immersion liquid is arranged on a supporting mount of larger diameter and possibly with a transparent base. For this supporting mount one can use for example in the simplest case just a conventional petri dish, for example with a diameter of 10 cm. As container for the immersion liquid one can likewise use a conventional vessel, for example a crystallizing dish, having a diameter of about 60 mm and a depth of about 35 mm.

Suitable dimensions for the damping float are, in the case of a Plexiglas tube, for example an external diameter of about 50 mm, an internal diameter of about 46 mm, a depth of about 17 mm and a thickness for the Plexiglas disc forming the base of about 1 mm. With these dimensions it has been found in practice that the crystallizing dish has to be filled to about two thirds full with the immersion liquid.

Because of the positioning of he different vessels one within the other one has no optical problems, i.e. it is not necessary to have optically precise surfaces, since normal irregularities do not occur. It is only necessary to use materials which are distortion-free from the outside, i.e. the final surface which faces towards the objective and the surface which faces the air must be optically flat.

BRIEF DESCRIPTION OF THE DRAWINGS

In order that the invention may be fully understood, one presently preferred embodiment of microscope in accordance with the invention will now be described by way of example and with reference to the accompanying drawings. In the drawings:

FIGS. 1(a) and (b) are front and side views respectively of a microscope in accordance with the invention;

DESCRIPTION OF THE PREFERRED EMBODIMENT

Figure 1:
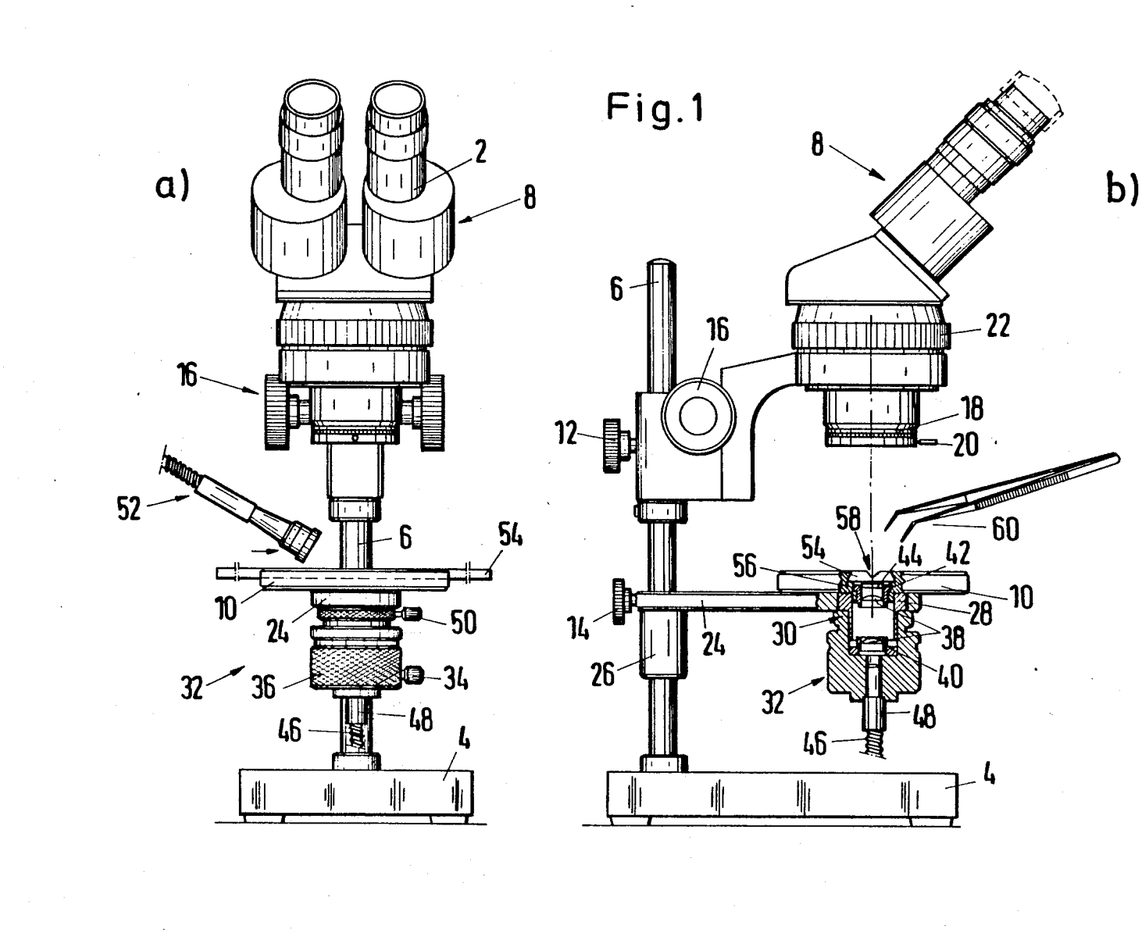

In the following, reference is first made to FIGS. 1(a) and 1(b). In the microscope of the present invention standard components are used so far as possible. In the embodiment which is shown by way of example in the drawings the microscope comprises two eyepieces 2. However, in the alternative, the invention could be embodied in a monocular microscope. In conventional manner, the microscope includes a base 4 and a stand 6 on which the eyepiece system 8 and a microscope stage 10 are mounted in known manner so as to be capable of height adjustment. Adjustment screws 12 and 14 are provided for setting the eyepiece system 8 and the microscope stage 10 respectively. Adjustment screws 16 serve to enable the eyepiece system 8 to be pivoted horizontally about the vertical axis of the stand. A zoom adjusting ring 22 on the eyepiece system 8 makes it possible to carry out stepless changes in the magnification of the microscope, which preferably, in standard manner, provides magnification between 10 and 50 times. A greater degree of magnification can be achieved by the use of conventional accessories. The eyepiece system also includes a polarization filter 18 at the end facing the specimen. This polarization filter is screwed into the eyepiece system and an adjusting pin 20 is provided for its adjustment.

The microscope stage 10 is, in the illustrated example, a standard circular stage which is mounted on a support plate 24. The support plate 24, which is guided on the stand 6 by means of a guide sleeve 26, has a recess which is centered with respect to the microscope stage 10 and in which is received a sleeve 30 which is provided with a flange 28. The sleeve 30 which extends downwards as a cylinder below the microscope stage 10 carries an objective unit 32 which embraces a light-receiving head which can be fixed in place by means of a screw 34. In this head are provided two condenser lenses 38 for concentrating the light rays, with the lower condenser lens resting on a pick-up plate 40. The upper condenser lens is gripped by a cylindrical sleeve 42 on which a filter plate 44 is seated. A bundle 46 of glass fibers in the form of a cable, with a cylindrical holder 48, is positioned below the condenser lens unit with the output end of the fiber bundle below the pick-up plate. The glassfiber bundle 46 is illuminated by a source of cold light which is not shown.

An additional arrangement for incident-light illumination is indicated at 52. In this arrangement one can likewise use a source of cold light of for example 100W as the light source. It is desirable to use for illumination by transmitted light or incident light a common light source which includes a device for screening out the parts of the beam which are not used in any particular case.

The microscope stage 10 is provided above the filter plate 44 with a dovetail guide in which, in the illustrated example, a correspondingly shaped slide-type specimen holder 54 of Plexiglas of Type 010 is inserted ("Plexiglas" is a Registered Trade Mark of Rohm GmbH in the Federal Republic of Germany). As can be seen from FIG. 1(b), the specimen holder 54 rests only along its edges on a bearing shoulder 56 of the dovetail guide extending in the longitudinal direction of the holder. In its upper face the specimen holder 54 is provided with an elongate recess 58 which extends in the lengthwise direction of the specimen holder and which has a wedge-shaped cross section. This recess serves to retain the gemstone or other specimen or object which is to be inspected. At 60 is indicated a pair of forceps for gripping and removing objects which have been selected or singled out.

Figure 2:
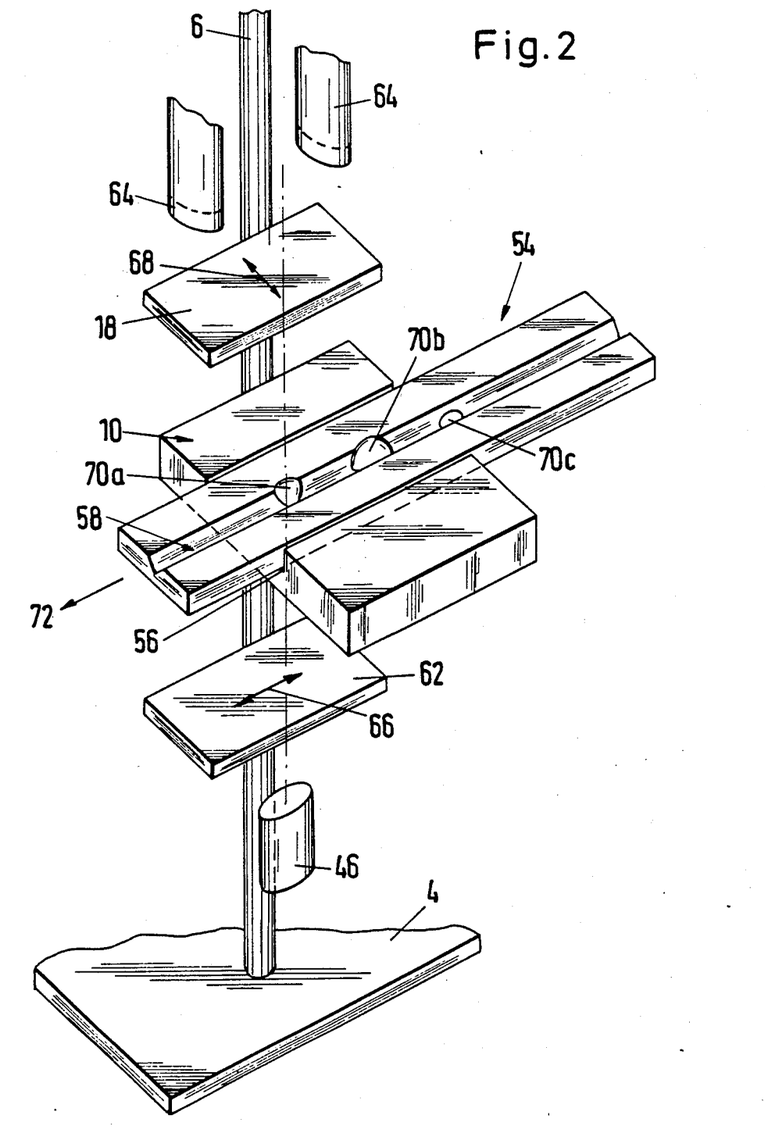
FIG. 2 is a schematic perspective view of a part of the microscope of FIG. 1.

FIG. 2 shows a part of the microscope of the present invention on an enlarged scale. Where components shown in FIG. 2 correspond to components shown also in FIGS. 1(a) and 1(b) these will not be described again. In FIG. 2 one can see, additionally, a second polarization filter 62 (polarizer). The two arrows 68 and 66 which are marked schematically on the polarization filters 18 and 62 respectively are intended to signify the crossed setting of the polarization filters by which gemstones 70a, 70b, 70c positioned in the recess 58 of the specimen holder 54 are examined. The arrow 72 indicates the displaceability of the specimen holder 54 in the dovetail guide of the microscope stage 10.

Figure 3:
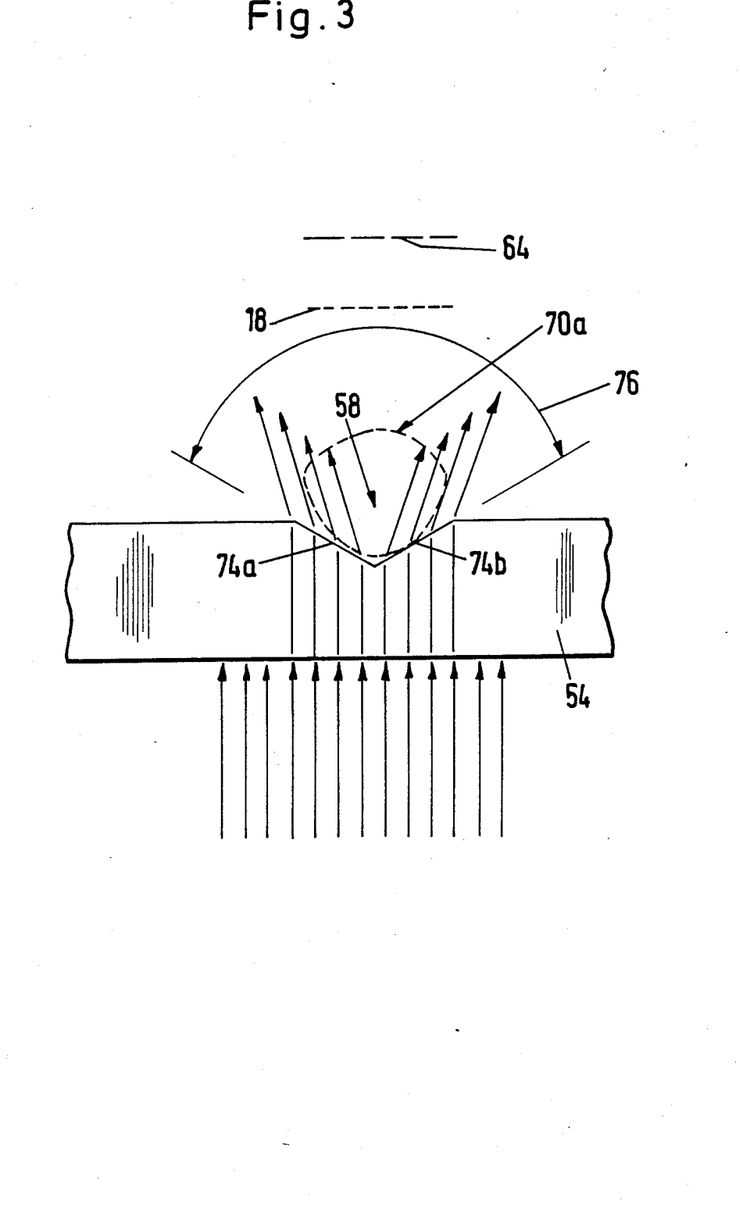
FIG. 3 is an illustration of the path of rays through the specimen holder and a gemstone.

FIG. 3 illustrates the path of the light rays in the region of the specimen holder 54. As is apparent from FIG. 3, the side faces 74a,74b of the wedge-shaped recess 58 form an angle 76 of approximately 120°. The gemstone 70a which is positioned in the recess 58, the polarization filter 18 and objective lenses 64 in the eyepiece system are only shown schematically.

The light rays from the glass-fiber bundle 46 strike the specimen holder 54 from below perpendicular to its surface. They then travel rectilinearly through the specimen holder 54. At the side faces 74a and 74b the light rays diverge outwardly at an angle to the vertical, according to the relationship of the refractive indices. The rays partially enter the gemstone 70a which in this way is illuminated from below and from the sides. The light rays which travel only through the specimen holder 54 pass outside the objective lenses 64, so that the specimen holder 54 appears dark to the observer. In the gemstone 70a the linearly-polarized light rays are elliptically polarized, so that even after the passage of the light through the gemstone 70a and through the polarization filter 18 light with sufficient brightness reaches the objective lenses 64. Because of the strong light source the intensity of this light is sufficient, even though it corresponds basically to about 10% of the intensity of the light which appears through a polarization filter after passage through double-refracting crystals. This explains the necessity for the strong light source in the examination of optically isotropic crystals and amorphous transparent materials, such as glass for example.

Figure 4:
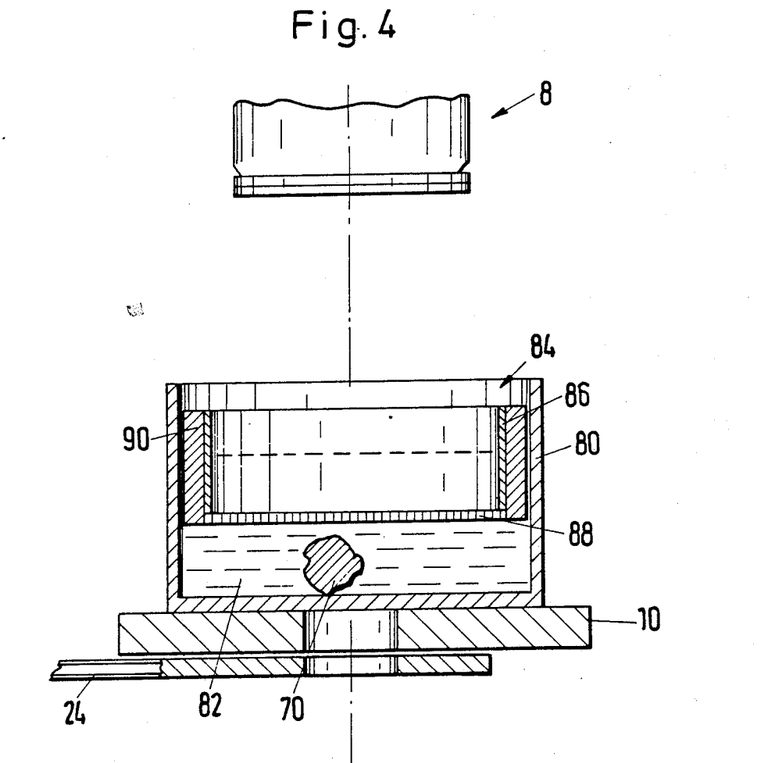
FIG. 4 is a partial sectional view through a device for the inspection of gemstones using an immersion liquid.

FIG. 4 shows a device which makes it possible to use a microscope in which the beam passes vertically for the examination of objects in an immersion liquid. In the illustrated example the microscope is constructed substantially as described above with reference to FIGS. 1(a), 1(b), 2 and 3. In FIG. 4 the microscope arrangement is therefore only partly shown. For greater clarity, essentially only the device for the immersion examination is shown, without the optical devices, etc. A microscope stage 10 is arranged on a support plate 24 which is connected to the microscope holder, in such a way as to be adjustable in terms of its height. The eyepiece system 8 is positioned spaced above the microscope stage. On the microscope stage 10 is positioned a vessel 80 containing the immersion liquid 82, with the vessel being arranged to be freely displaceable. Approximately in the center of the vessel 80, on its base, there is positioned an object 70 which is to be examined, in the illustrated embodiment an uncut gemstone.

A damping float 84, which in the illustrated embodiment is made of Plexiglas, is inserted into the immersion liquid 82. The damping float 84 consists of a cylindrical tubular member 86 and a base 88 which is secured thereto by adhesive for example. On the outside of the damping float are fixed four spacer ribs 90, only two of which are visible in the drawings.

This arrangement is extraordinarily simple and consists of very few components. It can easily be assembled and set up in the operational working state, and the substitution of objects to be examined can likewise be effected in a simple manner. Depending upon the chosen materials and relative densities the damping float 84 sinks into the immersion liquid, and any tilting or sticking of the damping float 84 is prevented by the spacer ribs 90. The damping float prevents optical faults arising from movement of the liquid surface and damps oscillations of the immersion liquid in the vessel 80.

I claim:

1. An apparatus for observing small objects, comprising:
   a lens,
   a cold light source,
   a translucent specimen holder between the light source and the lens, having an elongated recess on one side thereof for supporting therealong the small objects to be observed,
   a first polarization filter disposed between the lens and the holder and a second polarization filter disposed between the holder and the source, the first and second filters having respective polarization axes which are perpendicular to each other, and
   an optical fiber cable between the source and the second filter, for transmitting cold light from the source to the second filter so as to direct the light successively through the second filter, the holder, one of the objects, the first filter and the lens.

2. Apparatus according to claim 1, in which the cross-section of the recess narrows towards the bottom of the recess.

3. Apparatus according to claim 1, in which the material of the specimen holder is Plexiglass-brand polymethylmethacrylate of Type 010, and the recess is channel-shaped and has side walls which define a wedge-shaped cross section with an included angle of between 90° and 120°.

4. Apparatus according to claim 1, in which the material of the specimen holder is Plexiglas-brand polymethylmethacrylate of Type 072, and the recess is channel-shaped and has side walls which define a wedge-shaped cross section with an included angle of between 80° and 90°.

5. Apparatus according to claim 4, which includes an intermediate filter intermediate of the first and second polarization filters.

6. Apparatus according to claim 1, in which the material of the specimen holder is Plexiglas-brand polymethylmethacrylate of Type 010 and the recess is channel-shaped and has side walls which have a wedge-shaped cross section with an included angle of between 80° and 90°.

7. Apparatus according to claim 1, in which the specimen holder is of a slightly milky material and at least one of the underside of the specimen holder and side wall faces of the recess is matt.

8. Apparatus according to claim 1, in which at least one of the underside of the specimen holder and side wall faces of the recess is additionally dulled.

9. Apparatus according to claim 1, in which the recess in the specimen holder has a maximum width of 7 mm and a maximum depth of 3 mm.

10. Apparatus according to claim 1, which includes scale means associated with the recess.

11. Apparatus according to claim 1, in which the specimen holder has a length of the order of 30 cm, a width of the order of 3 cm and a depth of the order of 0.6 cm.

12. Apparatus according to claim 1, in which the specimen holder has a depth of the order of 0.7 cm and a thin plate having a width of the order of 4 cm is fixed to the upper surface of the specimen holder 13. Apparatus according to claim 1, which includes a microscope stage, and a dovetail-shaped guide for the specimen holder is provided in the microscope stage.

14. Apparatus according to claim 1, in which the configuration of the dovetail-shaped guide in the microscope stage is such that a pair of narrow supporting shoulders extend in the lengthwise direction adjacent to corner angles of the guide.

15. Apparatus according to claim 1, in which the specimen holder is provided on its underside, at the edges, with ribs forming contact bearing surfaces.

16. Apparatus according to claim 1, in which the cable comprises a bundle having a cross section in the range from 4 to 5 mm$^2$.

17. Apparatus according to claim 1, in which the cold light source is a halogen lamp.

18. Apparatus according to claim 1, in which a dimmer is provided for reducing the light intensity.

19. Apparatus according to claim 1, which includes means to provide incident-light illumination.

20. Apparatus according to claim 1, adapted for the examination of chains of pearls.

21. Apparatus according to claim 1, in which the material of the specimen holder is Plexiglas-brand polymethylmethacrylate of Type 072, and the recess is channel-shaped and has side walls which define a wedge-shaped cross section with an included angle of between 83° and 87°.

22. Apparatus according to claim 1, in which the material of the specimen holder is Plexiglas-brand polymethylmethacrylate of type 010 and the recess is channel-shaped and has side walls which have a wedge-shaped cross section with an included angle of between 83° and 87°.

23. Apparatus according to claim 1, in which the cable comprises a bundle having a cross section of 4.5 mm$^2$.

24. Apparatus according to claim 1, in which the material of the specimen holder is 66% translucent and polarized light is at least partially polarized after passing through it, and the recess is channel-shaped and has side walls which define a wedge-shaped cross section with an included angle of between 90° and 120°.

25. Apparatus according to claim 1, in which the material of the specimen holder is approximately 24% translucent and polarized light passing through it becomes diffuse and nonpolarized, and the recess is channel-shaped and has side walls which define a wedge-shaped cross section with an included angle of between 80° and 90°.

26. Apparatus according to claim 1, in which the material of the specimen holder is approximately 66% translucent and polarized light is at least partially polarized by passing through it, and the recess is channel-shaped and has side walls which have a wedge-shaped cross sections with an included angle of between 80° and 90°.

27. Apparatus according to claim 1, wherein the material of the specimen holder is polymethylmethacrylate.

28. Apparatus according to claim 1, wherein the material of the specimen holder is plastic.

29. Apparatus according to claim 28, wherein the plastic contains scattered particles which reduce the polarization of polarized light passing therethrough.

30. Apparatus according to claim 1, wherein the specimen holder contains scattered particles which reduce the polarization of polarized light passing therethrough.

31. Apparatus as in claim 1, wherein the specimen holder contains scattered particles diffuse and depolarize polarized light passing through it.

32. An apparatus as in claim 1, wherein said specimen holder is slidably displaceable between the light source and the lens in a direction of elongation of the recess.

33. An apparatus for observing small objects, comprising:
a lens,
a cold light source,
a slidably displaceable translucent plastic specimen holder between the light source and the lens, having an elongated recess on one side thereof for supporting therealong the small objects to be observed,
a first polarization filter disposed between the lens and the holder and a second polarization filter disposed between the holder and the source, the first and second filters having respective polarization axes which are perpendicular to each other, and
an optical fiber cable between the source and the second filter, for transmitting cold light from the source to the second filter so as to direct the light successively through the second filter, the holder, one of the objects, the first filter and the lens.

* * * * *